United States Patent
Gussen et al.

(10) Patent No.: US 10,011,176 B2
(45) Date of Patent: Jul. 3, 2018

(54) METHOD AND DEVICE FOR RECOGNISING THE CONDITION OF VEHICLE OCCUPANTS

(71) Applicants: FORD GLOBAL TECHNOLOGIES, LLC, Dearborn, MI (US); FORD-WERKE GMBH, Köln (DE)

(72) Inventors: Uwe Gussen, Huertgenwald/NRW (DE); Christoph Arndt Dr habil, Rheinland-Pfalz (DE); Frederic Stefan, Aachen/ NRW (DE)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 0 days.

(21) Appl. No.: 15/519,055

(22) PCT Filed: Jan. 14, 2016

(86) PCT No.: PCT/EP2016/050608
§ 371 (c)(1),
(2) Date: Apr. 13, 2017

(87) PCT Pub. No.: WO2016/116342
PCT Pub. Date: Jul. 28, 2016

(65) Prior Publication Data
US 2017/0225566 A1    Aug. 10, 2017

(30) Foreign Application Priority Data
Jan. 20, 2015    (DE) ........................ 10 2015 200 756

(51) Int. Cl.
*G08B 23/00*    (2006.01)
*B60K 28/06*    (2006.01)
(Continued)

(52) U.S. Cl.
CPC ............ *B60K 28/06* (2013.01); *A61B 5/0245* (2013.01); *A61B 5/1102* (2013.01); *A61B 5/18* (2013.01);
(Continued)

(58) Field of Classification Search
CPC .. A61B 5/18; A61B 5/02; A61B 5/024; A61B 5/0245; A61B 5/1102; A61B 5/725;
(Continued)

(56) References Cited

U.S. PATENT DOCUMENTS

2011/0066042 A1    3/2011    Pandia et al.
2011/0263994 A1*   10/2011   Burns ................ A61B 5/0006
                                                          600/509
(Continued)

FOREIGN PATENT DOCUMENTS

DE    10126224 A1    12/2002
DE    102011113100 A1    3/2013
(Continued)

OTHER PUBLICATIONS

Shin et al., "Heart rate variability analysis using a ballistocardiogram during Valsalva manoeuvre and post exercise", 2011 Institute of Physics and Engineering in medicine, published Jul. 8, 2011; Physiological Measurement, vol. 32, No. 8, downloaded from http://iopscience.iop.org/article/10.1088/0967-3334/32/8/015/meta.
(Continued)

*Primary Examiner* — Thomas Mullen
(74) *Attorney, Agent, or Firm* — Frank A. MacKenzie; Bejin Bieneman PLC

(57) ABSTRACT

The physical and/or mental condition of a vehicle occupant can be recognized on the basis of a BCG (ballistocardiograph) signal, which is obtained by means of a BCG sensor. The BCG sensor is an MEM sensor; a cross-correlation of
(Continued)

the BCG signal with heartbeat parameters is carried out in an optimum filter, which heartbeat parameters are varied within predefined limits to find a maximum of the cross-correlation function; and probable peaks are located in a cross-correlation function found in this manner and the heart rate is calculated therefrom.

20 Claims, 2 Drawing Sheets

(51) Int. Cl.
*A61B 5/11* (2006.01)
*G06F 17/15* (2006.01)
*A61B 5/00* (2006.01)
*A61B 5/18* (2006.01)
*A61B 5/0245* (2006.01)
*H03H 17/02* (2006.01)
*B60W 40/08* (2012.01)

(52) U.S. Cl.
CPC ............ *A61B 5/725* (2013.01); *A61B 5/7246* (2013.01); *G06F 17/15* (2013.01); *H03H 17/02* (2013.01); *A61B 2503/22* (2013.01); *B60W 2040/0872* (2013.01); *B60W 2040/0881* (2013.01)

(58) Field of Classification Search
CPC ....... A61B 5/7246; B60K 28/06; G06F 17/15; H03H 17/02
USPC ...... 340/425.5, 573.1, 576, 539.12; 600/300, 600/301, 481, 508
See application file for complete search history.

(56) References Cited

U.S. PATENT DOCUMENTS

| | | |
|---|---|---|
| 2012/0123279 A1 | 5/2012 | Brueser et al. |
| 2013/0158415 A1 | 6/2013 | Kim et al. |
| 2016/0354027 A1* | 12/2016 | Benson ................ A61B 5/0022 |
| 2017/0238847 A1* | 8/2017 | Inan ..................... A61B 5/1102 |

FOREIGN PATENT DOCUMENTS

| | | |
|---|---|---|
| DE | 102012111859 A1 | 2/2014 |
| EP | 1315451 B1 | 6/2005 |
| WO | WO 2016116342 A1 | 7/2016 |

OTHER PUBLICATIONS

English translation of EP International Search Report dated Feb. 29, 2016.

* cited by examiner

METHOD AND DEVICE FOR RECOGNISING THE CONDITION OF VEHICLE OCCUPANTS

CROSS-REFERENCE TO RELATED APPLICATIONS

This patent application is filed under 35 U.S.C. § 371 as a national stage of, and as such claims priority to, International Patent Application No. PCT/EP2016/050608, filed on Jan. 14, 2016, which claims priority to and all advantages of German Patent Application No. DE102015200756.1 filed on Jan. 20, 2016, each of the foregoing applications incorporated herein by reference in their entireties.

The present disclosure relates to a method and a device for recognizing the physical and/or mental condition of a vehicle occupant on the basis of a BCG (ballistocardiograph) signal, which is obtained by means of a BCG sensor.

Such a method and such a device are known from US 2013/0158415 A1. The BCG sensor here is a Wheatstone measuring bridge having strain gauges in a vehicle seat, from which a very high amount of noise may be expected at the low vibration amplitudes. The BCG signal thus obtained is compared to a pattern, which is selected from many patterns stored in a database. However, such a method requires a high level of computing effort, and it has been shown that usable results are also not available rapidly enough in this manner.

Recognizing the physical and/or mental condition of a vehicle occupant on the basis of ECG or EEG signals is known from DE 101 26 224 A1 and EP 1 315 451 B1, however, the signals have to be acquired by contact, i.e., via the skin resistance, which is complex and susceptible to error and/or can be annoying to the vehicle occupant.

A method is described in DE 10 2011 113 100 A1, in which a first BCG sensor acquires BCG signals of a vehicle occupant. A second BCG sensor is situated in a vibration-isolated manner in the vehicle seat and generates an interference reference for the BCG signal of the first sensor. To minimize the interference signals, the two signals are compared by means of an algorithm. However, the second BCG sensor means substantial additional technical expenditure.

An ECG measurement method is known from US 2011 006 6042 A1, in which the measured signals are stored and the present signal is compared to the stored signals. However, this method requires multiple ECG sensors and is therefore complex.

A vehicle seat is disclosed in DE 10 2012 111 859 A1, which has ECG sensors, BCG sensors, and PCG sensors. The signal of the sensor which has the highest accuracy is analyzed to monitor the heart rate of the passenger. This device is very technically complex due to the high number of the different sensors required.

The present disclosure includes a method and a device programmed to execute the method for identifying the physical and/or mental condition of a vehicle occupant rapidly, reliably, with as little amplifier and filter expenditure as possible, and without disturbing the vehicle occupant.

The BCG sensor in the context of the present disclosure is typically an MEM sensor, a micro-electrical-mechanical sensor, for example a spring-mass system, which acquires accelerations either by means of capacitance changes or in a piezoresistive manner.

Using MEM sensors for the remote acquisition of cardiac functions of patients by means of ballistocardiography is known from the magazine EL-Info Elektronik Informationen, issue November 2013, pages 68-70. Accordingly, it is supposed to be possible by means of filter algorithms (not described in greater detail) to extract the BCS signal from the resonance effects of a bed and from the noise, which can be realistic under the favorable conditions of an unmoving bed and a patient resting therein, but hardly in the extremely noisy situation in a driving vehicle.

The present inventors have discovered that better, more stable, and more rapid results are achieved using a BCG signal which is obtained by means of one or more MEM sensors in a vehicle if firstly a cross-correlation (convolution) of the BCG signal with heartbeat parameters is carried out in an optimum filter, also called a matched filter or correlation filter, which heartbeat parameters are varied within predefined limits to find a maximum of the cross-correlation function, and secondly probable peaks (i.e. local maxima) are located in a cross-correlation function found in such a manner and the heart rate is calculated therefrom.

The heartbeat parameters can simply be a number of heartbeat patterns, which are generated by frequency variation of one or more predefined basic heartbeat patterns within natural heartbeat limits. In a still simpler embodiment, the heartbeat patterns can be generated by frequency variation of a single predefined basic heartbeat pattern. In this manner, larger databases do not have to be searched.

The optimum filter therefore represents a time-variant optimum filter, which can be adapted to the pattern to be searched for in the noise of the sensor signal via parameters, for example the signal length and heart rate. This adaptation is achieved via the observation of the maximum of the cross-correlation function. Variations in the parameters can be taken directly from the filtered results in the settled state (parameters fixed for a point in time).

In one embodiment, the maximum of the cross-correlation function is found by short-term interval cross-correlation of the BCG signal with the generated heartbeat patterns with respect to the variation frequency.

According to the present disclosure, a search is not performed in a large database and adaption is not then again performed, as in the prior art which forms the species, but rather a predefined signal is varied over a parameter space until the peak amplitude is optimized.

To reduce the computing effort still more, the BCG signal can be subjected to an adaptive window function which is dependent on the length of the heartbeat pattern, after the maximum of the cross-correlation function has been found and before the probable peaks are located.

Optionally, a separate perimeter adaptation can additionally be carried out to further optimize the peak amplitude. In both cases, the parameters can be continuously adapted, which is not possible in the case of a database search of patterns as a result of limited size. The optional window function and parameter adaptation act as filters which remove incorrectly recognized peaks.

The BCG sensor has to be capable of acquiring the vibrations in the aorta of a vehicle occupant, which are transmitted via his body. For this purpose, the BCG sensor is preferably installed in a vehicle seat, which is generally the driver's seat, but it could possibly also be located somewhere else, for example in a steering wheel. Moreover, in addition to the driver's seat, further vehicle seats can be equipped with BCG sensors, to monitor the condition of the persons seated thereon.

As parameters for estimating the physical and/or mental condition of a vehicle occupant, not only his heart rate but also his blood pressure can be ascertained by means of the method, in particular because the peak amplitudes are correlated with the blood pressure, wherein there is also a certain relationship between heart rate and blood pressure, however.

The disclosed systems and methods provide for rapid, reliable, and incomplex monitoring of the physical and/or mental condition of vehicle occupants, which does not disturb them in any way and which enables, for example, a driver to be warned in case of fatigue, stress, illness, medication side effects, allergic shocks, or body dehydration and to recommend countermeasures if necessary, for example to take a stop or also to inform an emergency service provider via radio. For this purpose, the disclosed systems and methods can be combined with other techniques for recognizing the physical and/or mental condition of drivers, for example those which analyze driver reactions to specific traffic situations.

To calibrate a system in which the disclosed method is carried out, it can be adapted to different damping and rigidity parameters of a vehicle seat such that different seat damping and support coefficients are recognized, stored, and taken into consideration. Therefore, the method can be carried out easily in any arbitrary vehicle, entirely independently of the respective seat construction (damping structure as a result of different materials; different seat adaptation, for example sport mode, comfort mode, etc.; or even if seat parameters temporarily change, for example as a result of seat heating or cooling). The disclosure therefore has simple portability to different vehicles and seat concepts.

A description of exemplary embodiments on the basis of the drawings follows. In the figures.

Figure 1:
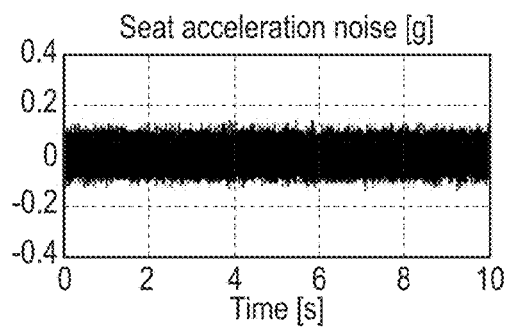
FIG. 1 shows example signals which are acquired, generated, processed and/or calculated in the scope of the ballistocardiographic heartbeat recognition.

The signals shown in FIGS. 1 to 6 are the following signals, which are simulated on the basis of realistic values:

FIG. 1 shows typical seat acceleration noise in a vehicle seat, having a mean amplitude of approximately 0.1 g during travel and over a time of 10 seconds.

Figure 2:
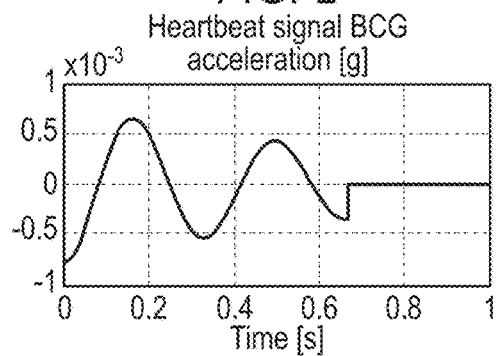
FIG. 2 shows a further example of signals which are acquired, generated, processed and/or calculated in the scope of the ballistocardiographic heartbeat recognition.

FIG. 2 shows the amplitude of a heartbeat signal, as it arrives at a BCG seat sensor, having a maximum amplitude of approximately 0.0005 g and over a time of 1 second. The signal has the form of a damped cosine function, wherein the form of the damping is not relevant here.

Figure 3:
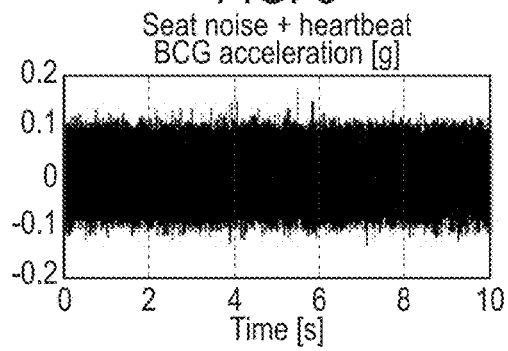
FIG. 3 shows a further example of signals which are acquired, generated, processed and/or calculated in the scope of the ballistocardiographic heartbeat recognition.

FIG. 3 shows the sum of the signals acquired by the BCG seat sensor from FIGS. 1 and 2 over a time of 10 seconds.

Figure 4:
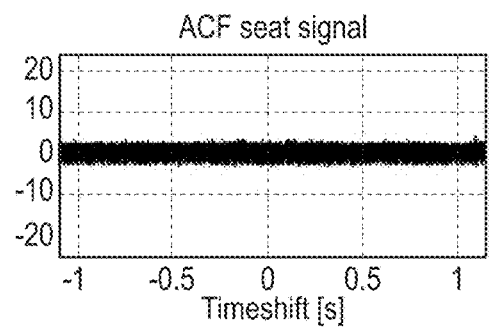
FIG. 4 shows a further example of signals which are acquired, generated, processed and/or calculated in the scope of the ballistocardiographic heartbeat recognition.

FIG. 4 shows the autocorrelation function of the seat signal from FIG. 1, i.e. the correlation of the signal with itself, with the time and/or phase shift on the abscissa.

Figure 5:
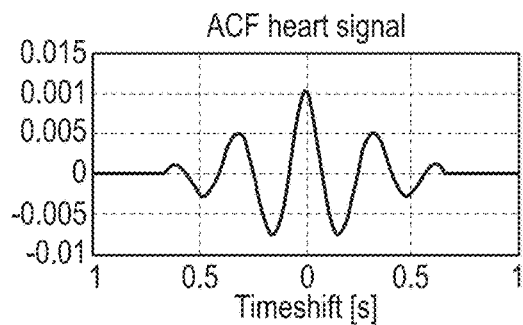
FIG. 5 shows a further example of signals which are acquired, generated, processed and/or calculated in the scope of the ballistocardiographic heartbeat recognition.

FIG. 5 shows the autocorrelation function of the heartbeat signal from FIG. 2.

Figure 6:
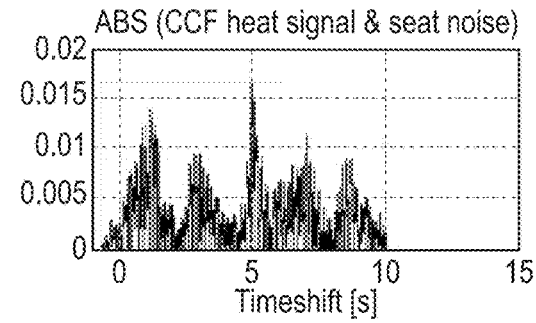
FIG. 6 shows a further example of various signals which are acquired, generated, processed and/or calculated in the scope of the ballistocardiographic heartbeat recognition.

FIG. 6 shows the absolute value of the cross-correlation of the sum of seat noise and heartbeat signal acquired by the BCG seat sensor.

The amplitude in the recognition process is dependent on two influences, namely firstly the noise procedure during the seat measurement (inherent noise and noise induced by the road and the driver) and secondly the length and amplitude (energy) of the heartbeat signal.

Figure 7:
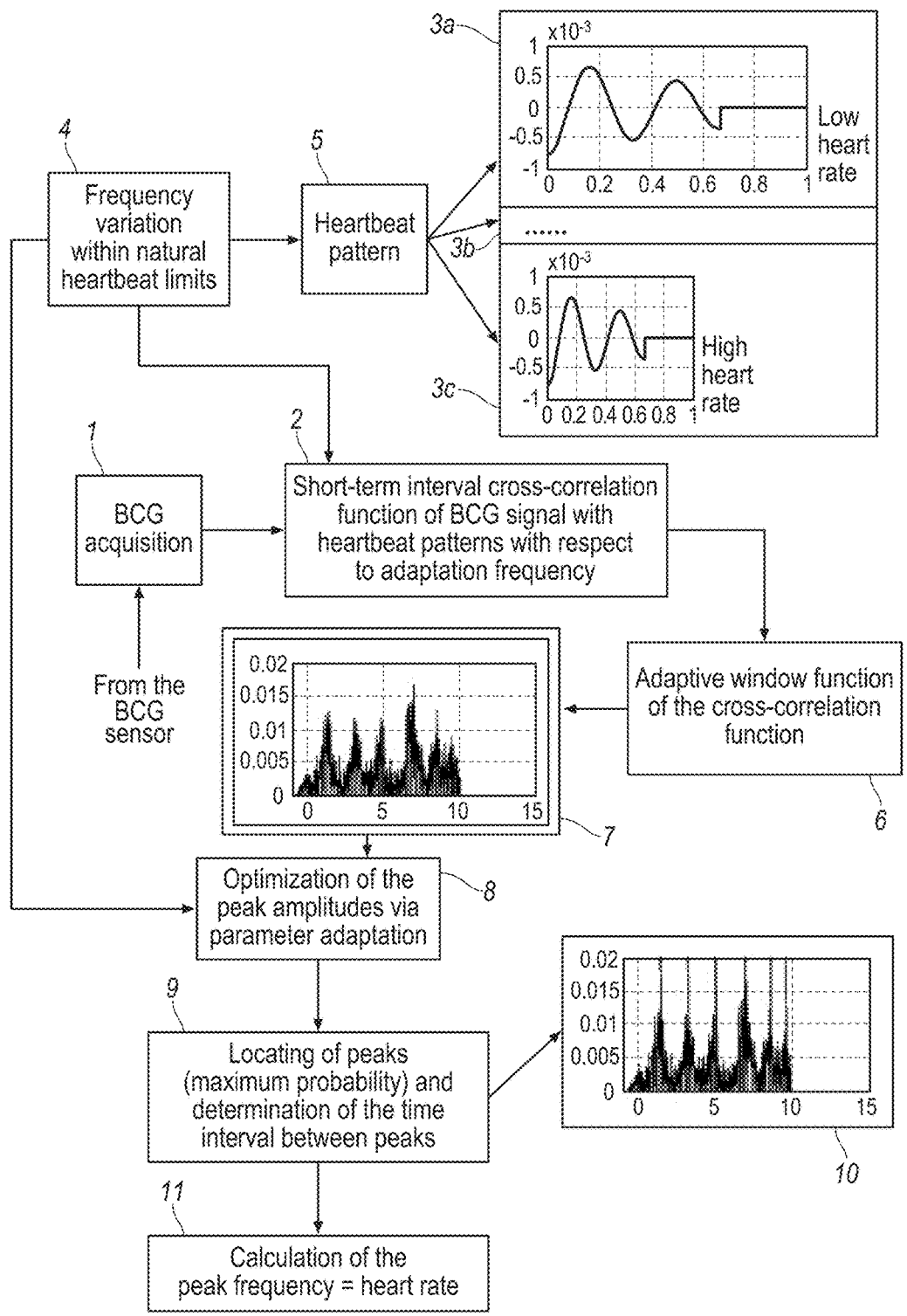
FIG. 7 shows a block diagram to explain the ballistocardiographic heartbeat recognition.

FIG. 7 is a block diagram to explain the ballistocardiographic heartbeat recognition in a motor vehicle. In block 1, a BCG signal is continuously detected by a seat sensor and supplied to a block 2 in intervals which correspond to short time intervals.

Block 2 represents an optimum filter, which carries out a short-term interval cross-correlation (CCF) of the BCG signal using various heartbeat patterns $3a, \ldots, 3b, \ldots, 3c$, which correspond to different heart rates and which are generated by frequency variation of a predefined heartbeat pattern 5 within natural heartbeat limits. For this purpose, the optimum filter 2 also receives the respective adaptation frequency of the frequency variation performed in block 4.

The cross-correlation function obtained in block 2 is subjected in block 6 to an adaptive window function depending on the length of the heartbeat pattern and the measured BCG signal, in order to limit the computing effort.

After carrying out the adaptive window function, the absolute value of the cross-correlation of the measured sum of seat noise and heartbeat signal is obtained, as shown in block 7 and in FIG. 6.

For the signal form shown in block 7, a separate parameter adaptation is also carried out in block 8 to optimize the peak amplitudes, before, in block 9, the peaks are located in the signal form (according to maximum probability) and the time interval between adjacent peaks is ascertained, as illustrated in block 10.

The peak frequency, which represents the heart rate of the vehicle occupant, then results therefrom in block 11.

This heart rate is not a smooth signal and therefore requires a further filter (not shown) to eliminate outliers, which result from nonrecognition of peaks in the cross-correlation function. Such a filter can be a mean value filter or a Kalman filter with residual regulation, which are both capable of eliminating atypical measurements in real time.

On the basis of the smoothed heart rate of the vehicle occupant, his physical and/or mental condition can now be concluded, as is known per se.

The above-described method contains the two following essential method steps: firstly the frequency variation of a predefined heartbeat pattern and the maximization of peak amplitudes by means of correlation of different heartbeat patterns with a measured BCG signal; and secondly peak identification, peak location, and ascertainment of the heart rate.

The invention claimed is:

1. A method for identifying a condition of a vehicle occupant on the basis of ballistocardiograph (BCG) data, comprising:
obtaining the BCG data of the vehicle occupant from a BCG sensor, wherein the BCG sensor is a micro-electrical-mechanical (MEM) sensor;
carrying out a cross-correlation function of a BCG signal with heartbeat parameters in an optimum filter, wherein the heartbeat parameters are varied within predefined limits to find a maximum of the cross-correlation function;
locating probable peaks in the cross-correlation function;
calculating a heart rate from the probable peaks; and wherein the heartbeat parameters include a plurality of heartbeat patterns that are generated by frequency variation of one or more predefined heartbeat patterns within natural heartbeat limits.

2. The method of claim 1, wherein the heartbeat parameters include a plurality of heartbeat patterns that are generated by frequency variation of a single predefined heartbeat pattern within natural heartbeat limits.

3. The method of claim 1, wherein a maximum of the cross-correlation function is found by short-term interval cross-correlation of the BCG signal with the generated heartbeat patterns.

4. The method of claim 1, wherein, after a maximum of the cross-correlation function has been found and before the probable peaks are located, the BCG signal is subjected to an adaptive window function.

5. The method of claim 1, wherein, after at least one of (a) the maximum of the cross-correlation function has been found and (b) an adaptive window function has been applied, and before the probable peaks are located, a separate parameter adaptation is carried out to optimize the peak amplitudes.

6. The method of claim 1, wherein located peaks are filtered to exclude unrecognized peaks from the calculation of the heart rate.

7. The method of claim 1, wherein the BCG sensor is a seat sensor.

8. The method of claim 1, further comprising determining a blood pressure of the vehicle occupant in addition to the heart rate.

9. The method of claim 1, wherein a first seat damping coefficient and a second support coefficient are used to obtain the heart rate.

10. A system, comprising:
a ballistocardiograph (BCG) sensor, wherein the BCG sensor is a micro-electrical-mechanical (MEM) sensor; and
a computing device programmed to
obtain the BCG data of a vehicle occupant from the BCG sensor;
carry out a cross-correlation function of a BCG signal with heartbeat parameters in an optimum filter, wherein the heartbeat parameters are varied within predefined limits to find a maximum of the cross-correlation function;
locate probable peaks in the cross-correlation function;
calculate a heart rate from the probable peaks; and
wherein the computing device is further programmed to include in the heartbeat parameters a plurality of heartbeat patterns that are generated by frequency variation of one or more predefined heartbeat patterns within natural heartbeat limits.

11. The system of claim 10, the computing device further programmed to include in the heartbeat parameters a plurality of heartbeat patterns that are generated by frequency variation of a single predefined heartbeat pattern within natural heartbeat limits.

12. The system of claim 10, the computing device further programmed to find a maximum of the cross-correlation function by short-term interval cross-correlation of the BCG signal with the generated heartbeat patterns.

13. The system of claim 10, the computing device further programmed to, after a maximum of the cross-correlation function has been found and before the probable peaks are located, subject the BCG signal subjected to an adaptive window function.

14. The system of claim 10, the computing device further programmed to, after at least one of (a) the maximum of the cross-correlation function has been found and (b) an adaptive window function has been applied, and before the probable peaks are located, carry out a separate parameter adaptation to optimize the peak amplitudes.

15. The system of claim 10, the computing device further programmed to filter located peaks to exclude unrecognized peaks from the calculation of the heart rate.

16. The system of claim 10, wherein the BCG sensor is a vehicle seat sensor.

17. The system of claim 10, the computing device further programmed to determine a blood pressure of a vehicle occupant in addition to the heart rate.

18. The system of claim 10, the computing device further programmed to use a first seat clamping coefficient and a second support coefficient to obtain the heart rate.

19. A method for identifying a condition of a vehicle occupant on the basis of ballistocardiograph (BCG) data, comprising:
obtaining the BCG data of the vehicle occupant from a BCG sensor, wherein the BCG sensor is a micro-electrical-mechanical (MEM) sensor;
carrying out a cross-correlation function of a BCG signal with heartbeat parameters in an optimum filter, wherein the heartbeat parameters are varied within predefined limits to find a maximum of the cross-correlation function;
locating probable peaks in the cross-correlation function;
calculating a heart rate from the probable peaks; and
wherein a maximum of the cross-correlation function is found by short-term interval cross-correlation of the BCG signal with the generated heartbeat patterns.

20. A system, comprising:
a ballistocardiograph (BCG) sensor, wherein the BCG sensor is a micro-electrical-mechanical (MEM) sensor; and
a computing device programmed to
obtain the BCG data of a vehicle occupant from the BCG sensor;
carry out a cross-correlation function of a BCG signal with heartbeat parameters in an optimum filter, wherein the heartbeat parameters are varied within predefined limits to find a maximum of the cross-correlation function;
locate probable peaks in the cross-correlation function;
calculate a heart rate from the probable peaks; and
find a maximum of the cross-correlation function by short-term interval cross-correlation of the BCG signal with the generated heartbeat patterns.

* * * * *